(12) United States Patent
Arnold et al.

(10) Patent No.: US 11,559,246 B2
(45) Date of Patent: *Jan. 24, 2023

(54) HEALTH MONITORING DEVICE

(71) Applicants: KNOW BIOLOGICAL, INC., Milton, GA (US); National Technology & Engineering Solutions of Sandia, LLC, Albuquerque, NM (US)

(72) Inventors: Gary Stephen Arnold, Cumming, GA (US); Matthew Wallace Moorman, Albuquerque, NM (US); Joshua Jonathan Whiting, Albuquerque, NM (US)

(73) Assignees: Know Biological, Inc., Milton, GA (US); National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/340,195

(22) Filed: Jun. 7, 2021

(65) Prior Publication Data
US 2021/0338142 A1    Nov. 4, 2021

Related U.S. Application Data

(60) Continuation-in-part of application No. 17/242,441, filed on Apr. 28, 2021, now Pat. No. 11,272,875,
(Continued)

(51) Int. Cl.
*A61B 5/00* (2006.01)
*A61B 10/00* (2006.01)
(Continued)

(52) U.S. Cl.
CPC ........ *A61B 5/4094* (2013.01); *A61B 5/14546* (2013.01); *A61B 5/443* (2013.01);
(Continued)

(58) Field of Classification Search
CPC ..... A61B 5/4094; A61B 5/443; A61B 5/6833; G01N 30/00; G01N 2030/025
See application file for complete search history.

(56) References Cited

U.S. PATENT DOCUMENTS

| 5,036,861 A * | 8/1991 | Sembrowich ......... A61N 1/325 604/20 |
| 5,281,397 A * | 1/1994 | Ligon ................ G01N 30/7206 422/89 |

(Continued)

FOREIGN PATENT DOCUMENTS

| WO | 2020232349 | 11/2020 |
| WO | 2021050678 | 3/2021 |

OTHER PUBLICATIONS

Davis, The Investigation of Human Scent from Epileptic Patients for the Identification of a Biomarker for Epileptic Seizures, Oct. 31, 2017, Florida International University (see title and abstract) (Year: 2017).*

(Continued)

*Primary Examiner* — Puya Agahi
(74) *Attorney, Agent, or Firm* — Taylor English Duma LLP

(57) ABSTRACT

Example aspects of a volatile organic compound detection device, a wearable health monitoring device, and a method of monitoring a user's health are disclosed. The volatile organic compound detection device can comprise a collector comprising a collector material configured to collect volatile organic compounds given off from a user's skin; a separator comprising a gas chromatography column configured to separate mixtures of the volatile organic compounds into their constituent chemicals; and an identifier comprising a detector and a processor, the detector configured to transduce the constituent chemicals into a signal, the processor (Continued)

configured to process the signal to identify specific volatile organic compounds indicative of a health condition.

19 Claims, 3 Drawing Sheets

Related U.S. Application Data which is a division of application No. 16/874,229, filed on May 14, 2020, now Pat. No. 11,020,042.

(60) Provisional application No. 62/848,319, filed on May 15, 2019.

(51) Int. Cl.
| | |
|---|---|
| *G01N 30/64* | (2006.01) |
| *G01N 30/20* | (2006.01) |
| *G01N 30/80* | (2006.01) |
| *G01N 30/00* | (2006.01) |
| *G01N 30/60* | (2006.01) |
| *A61B 5/145* | (2006.01) |
| *G01N 30/02* | (2006.01) |

(52) U.S. Cl.
CPC .......... *A61B 5/6831* (2013.01); *A61B 5/6833* (2013.01); *A61B 10/00* (2013.01); *G01N 30/00* (2013.01); *G01N 30/20* (2013.01); *G01N 30/60* (2013.01); *G01N 30/64* (2013.01); *G01N 30/80* (2013.01); *A61B 2010/0083* (2013.01); *G01N 2030/025* (2013.01)

(56) References Cited

U.S. PATENT DOCUMENTS

| | | | |
|---|---|---|---|
| 6,666,907 B1 | 12/2003 | Manginell et al. | |
| 6,699,392 B1 | 3/2004 | Manginell et al. | |
| 7,118,712 B1 | 10/2006 | Manginell et al. | |
| 7,155,812 B1 | 1/2007 | Peterson et al. | |
| 10,151,732 B1 | 12/2018 | Moorman et al. | |
| 10,161,835 B1 | 12/2018 | Moorman et al. | |
| 11,020,042 B2 | 6/2021 | Arnold et al. | |
| 11,272,875 B2 | 3/2022 | Arnold et al. | |
| 2007/0027383 A1* | 2/2007 | Peyser ................. | A61B 5/1486 600/347 |
| 2008/0146890 A1 | 6/2008 | Leboeuf et al. | |
| 2011/0259081 A1* | 10/2011 | Chou ................... | G01N 30/463 73/23.42 |
| 2013/0328697 A1* | 12/2013 | Lundy .................... | G08B 21/02 340/870.01 |
| 2016/0015315 A1 | 1/2016 | Auphan et al. | |
| 2016/0103104 A1 | 4/2016 | Gianchandani et al. | |
| 2016/0194590 A1 | 7/2016 | Loboda | |
| 2017/0027482 A1 | 2/2017 | Zilberstein et al. | |
| 2017/0035622 A1 | 2/2017 | Wang | |
| 2017/0119279 A1 | 5/2017 | Ahmad et al. | |
| 2017/0209313 A1* | 7/2017 | Letourneau ........... | G01N 21/78 |
| 2017/0248524 A1 | 8/2017 | Le | |
| 2018/0042585 A1 | 2/2018 | Heikenfeld | |
| 2018/0153451 A1 | 6/2018 | Heikenfeld et al. | |
| 2018/0160909 A1* | 6/2018 | Damania ................ | G01K 1/024 |
| 2018/0256137 A1 | 9/2018 | Heikenfeld et al. | |
| 2019/0021674 A1 | 1/2019 | Brewer, Jr. et al. | |
| 2019/0030230 A1* | 1/2019 | Connor ............... | A61M 60/148 |
| 2019/0099009 A1* | 4/2019 | Connor ................... | A61B 5/398 |
| 2019/0254641 A1 | 8/2019 | Begtrup et al. | |
| 2020/0008756 A1* | 1/2020 | Nishiyama ............ | A61B 5/441 |
| 2020/0330011 A1 | 10/2020 | Honore et al. | |
| 2020/0337594 A1 | 10/2020 | Reddy | |
| 2020/0359955 A1 | 11/2020 | Arnold et al. | |
| 2021/0085295 A1* | 3/2021 | Fehr ..................... | A61B 5/0075 |
| 2021/0251560 A1 | 8/2021 | Arnold et al. | |
| 2021/0282678 A1 | 9/2021 | Haick et al. | |
| 2021/0321934 A1 | 10/2021 | Arnold et al. | |
| 2022/0142557 A1 | 5/2022 | Arnold et al. | |

OTHER PUBLICATIONS

Arnold, Gary Stephen; Requirement for Restriction/Election for U.S. Appl. No. 17/242,441, filed Apr. 28, 2021, dated Sep. 1, 2021, 6 pgs.
Arnold, Gary Stephen; Notice of Allowance for U.S. Appl. No. 17/242,441, filed Apr. 28, 2021, dated Oct. 26, 2021, 20 pgs.
Arnold, Gary Stephen; Non-Final Office Action for U.S. Appl. No. 17/308,145, filed May 5, 2021, dated Nov. 30, 2021, 18 pgs.
Arnold, Gary Stephen; Notice of Allowance for U.S. Appl. No. 17/308,145, filed May 5, 2021, dated Oct. 25, 2021, 16 pgs.
Davis, The Investigation of Human Scent from Epileptic Patients for the Identification of a Biomarker for Epileptic Seizures, Florida International University, Oct. 31, 2017. (Year 2017), 171 pgs.
Arnold, Gary Stephen; International Preliminary Report on Patentability for PCT Application No. PCT/US20/33120, filed May 15, 2020, dated Nov. 25, 2021, 7 pgs.
Arnold, Gary Stephen; Notice of Allowance for U.S. Appl. No. 17/242,441, filed Apr. 28, 2021, dated Nov. 12, 2021, 15 pgs.
Arnold, Gary Stephen; Final Office Action for U.S. Appl. No. 17/308,145, filed May 5, 2021, dated Mar. 10, 2022, 15 pgs.
Arnold, Gary Stephen; Non-Final Office Action for U.S. Appl. No. 17/568,799, filed Jan. 5, 2022, dated Mar. 31, 2022, 20 pgs.
Arnold, Gary Stephen; Notice of Allowance for U.S. Appl. No. 16/874,229, filed May 14, 2020, dated Apr. 27, 2021, 211 pgs.
Arnold, Gary Stephen; Requirement for Restriction/Election for U.S. Appl. No. 16/874,229, filed May 14, 2020, dated Mar. 3, 2021, 7 pgs.
Davis, The Investigation of Human Scent from Epileptic Patients for the Identification of a Biomarker for Epileptic Seizures, (https://digitalcommons.fiu.edu/cgi/viewcontenl.cgi?article=4611&context=etd), Florida International University, Oct. 31, 2017. (Year: 2017).
Maa et al., Canine detection of volatile organic compounds unique to human epileptic seizure, (hllps://www.sciencedirect.com/science/article/pii/S1525505020308702), Epilepsy and Behavior, Dec. 23, 2020. (Year: 2020).
Zamkah et al., Identification of Suitable Biomarkers for Stress and Emotion Detection for Future Personal Affective Wearable Sensors, (hllps://www.ncbi.nlm.nih.gov/pmc/articles/PMC7235866/), Biosensors, Apr. 16, 2020. (Year: 2020).
Arnold, Gary Stephen; Non-Final Office Action for U.S. Appl. No. 17/308,145, filed May 5, 2021, dated Jul. 8, 2021, 185 pgs.
Arnold, Gary Stephen; International Search Report and Written Opinion for PCT Application No. PCT/US20/33120, filed May 15, 2020, dated Aug. 19, 2020, 8 pgs.
Arnold, Gary Stephen; Non-Final Office Action for U.S. Appl. No. 17/308,145, filed May 5, 2021, dated Jun. 28, 2022, 22 pgs.
Arnold, Gary Stephen; Final Office Action for U.S. Appl. No. 17/568,799, filed Jan. 5, 2022, dated Jul. 27, 2022, 16 pgs.
Arnold, Gary Stephen; Applicant-Initiated Interview Summary for U.S. Appl. No. 17/308,145, filed May 5, 2021, dated Sep. 20, 2022, 2 pgs.
Arnold, Gary Stephen; Final Office Action for U.S. Appl. No. 17/308,145, filed May 5, 2021, dated Oct. 20, 2022, 23 pgs.
Arnold, Gary Stephen; Notice of Allowance for U.S. Appl. No. 17/568,799, filed Jan. 5, 2022, dated Oct. 18, 2022, 12 pgs.
Arnold, Gary Stephen; Extended European Search Report for application No. 22176201.6, filed May 30, 2022, dated Oct. 13, 2022, 9 pgs.
Roodt, et al.; Article entitled: "Human skin volatiles: Passive sampling and Go X GC-ToFMS analysis as a tool to investigate the skin microbiome and interactions with anthropophilic mosquito disease vectors", Journal of Chromatography B 1097-1098 (2018) 83-93, 11 pgs.

* cited by examiner

HEALTH MONITORING DEVICE

CROSS-REFERENCE TO RELATED APPLICATIONS

The present application is a continuation-in-part of U.S. application Ser. No. 17/242,441, filed Apr. 28, 2021, which is a divisional of U.S. application Ser. No. 16/874,229, filed May 14, 2020 and which issued as U.S. Pat. No. 11,020,042 on Jun. 1, 2021, which claims the benefit of U.S. Provisional Application No. 62/848,319, filed May 15, 2019, all of which are hereby specifically incorporated by reference herein in their entireties.

STATEMENT OF GOVERNMENT INTEREST

This invention was made with government support under Contract No. DE-NA0003525 awarded by the United States Department of Energy/National Nuclear Security Administration. The government has certain rights in the invention.

TECHNICAL FIELD

This disclosure relates to medical devices. More specifically, this disclosure relates to a seizure detection device.

BACKGROUND

Epilepsy is the most common neurological disorder in the world after migraine, stroke, and Alzheimer's disease. It is a disorder of the central nervous system, not caused by an underlying, treatable medical condition, characterized by recurring periods of altered brain function caused by abnormal or excessive electrical discharges in the brain, resulting in what is commonly called a seizure. It is one of the world's oldest recognized health conditions, with recorded occurrences dating back to 4,000 BC.

Worldwide, there are nearly 65 million people who have epilepsy, with more than 3.5 million in the U.S. alone. Worldwide, there are 2.4 million new cases of epilepsy each year, with more than 150,000 new cases each year in the U.S. alone. Over a lifetime, more than one in twenty-six people with be diagnosed with the disease. Medication and medical intervention can control seizures in approximately two-thirds of patients, with the remaining one-third experiencing uncontrolled and unpredictable seizure episodes. There are estimated to be nearly one million deaths directly related to epilepsy each year worldwide, including some 50,000 deaths in the U.S each year.

Each year, approximately 80 people out of every 100,000 in the general population will experience new-onset seizures, and approximately 60% of these will have repeated episodes leading to the diagnosis of epilepsy. Misunderstanding, prejudice, and social humiliation have always surrounded epilepsy. This continues in most countries today and can significantly impact the quality of life for people with epilepsy.

The social consequences of epilepsy are often more impactful than the seizures themselves. The lack of predictability inherent in epilepsy is devastating. Never knowing when a seizure might strike imposes major limitations in family, social, educational, and vocational activities. In addition to the potential of serious injury from falls and other accidents during seizures, the societal stigma attached to epilepsy and its unpredictability that can cause significant demoralization, irritation, and anxiety. Frustratingly, studies have shown that increased anxiety can lead to increased incidence of seizures, and increased seizures can lead to an even greater increase in chronic anxiety.

In summation, unexpected seizures can result in accident, injury, embarrassment, and costly trips to the emergency room. They can be difficult to predict and can be dangerous, particularly in instances where the patient is unable to contact family, a friend, or medical personnel when needed. Furthermore, patients often must take daily prophylactic medications that can be toxic and can be accompanied by unpleasant, occasionally life-threatening side effects.

Additionally, a person's health can be assessed through a set of well-defined biomarkers including exudates, such as volatile organic compounds (VOCs), blood oxygenation, pulse, heart rate variability, body temperature. Every day the human body emits various VOCs through exhalation breath and bodily fluids, such as sweat and saliva. The specific types of VOCs emitted, and the concentrations thereof can be indicative of specific health concerns.

Volatile organic compounds (VOCs) are gaseous, organic molecules that have a high vapor pressure at room temperature, which relates to a low boiling point. Research indicates more than 1,850 different VOCs can be found in the human body. These compounds are both endogenously produced by the body itself and exogenously introduced from environmental sources. The presence and concentrations of VOCs provides significant insight into the health of the host organism. Specific VOC bouquets are diagnostically relevant as they are indicative of existing or developing health concerns.

For example, in addition to the nearly 65 million people who have epilepsy, there are more than one billion people who suffer from chronic migraines, multiple billions that experience extreme, debilitating stress, and millions who contract new varieties of viral and bacterial infections each year, such as COVID-19. Unexpected or undiagnosed medical conditions can result in accident, injury, costly trips to the emergency room, and substantial increase in medical costs across the range of health concerns.

SUMMARY

It is to be understood that this summary is not an extensive overview of the disclosure. This summary is exemplary and not restrictive, and it is intended neither to identify key or critical elements of the disclosure nor delineate the scope thereof. The sole purpose of this summary is to explain and exemplify certain concepts of the disclosure as an introduction to the following complete and extensive detailed description.

Disclosed is a collector for a seizure detection device comprising a collector material configured to collect volatile organic compounds given off from a patient's skin; a wrapping configured to isolate the collector material from an external environment; a heater comprising a heating element, the heating element configured to emit a thermal pulse to desorb the volatile organic compounds from the collector material; and a mesh layer configured to prevent the collector material from contacting the patient's skin, wherein the collector material is received between the wrapping and the mesh layer.

Also disclosed is a seizure detection device comprising a collector comprising a collector material configured to collect volatile organic compounds given off from a patient's skin; a separator comprising a gas chromatography column, the gas chromatography column comprising a chemically-selective film, wherein mixtures of the volatile organic compounds are configured to elute from the collector and to diffuse into and out of the chemically-selective film to separate the mixtures into their constituent chemicals; and an identifier comprising a detector and a processor, the detector configured to receive, ionize, and detect the constituent chemicals eluting from the gas chromatography column, the processor configured to process information about the ionized chemicals to identify volatile organic compounds indicative of a seizure.

Also disclosed is a method of detecting a seizure comprising collecting volatile organic compounds with a collector material of a collector; separating each of the volatile organic compounds into its constituent chemicals with a gas chromatography column; ionizing the constituent chemicals to create ionized chemicals and detecting the ionized chemicals; and analyzing the ionized chemicals to identify seizure-indicative volatile organic compounds.

Disclosed is a volatile organic compound detection device comprising a collector comprising a collector material configured to collect volatile organic compounds given off from a user's skin; a separator comprising a gas chromatography column configured to separate mixtures of the volatile organic compounds into their constituent chemicals; and an identifier comprising a detector and a processor, the detector configured to transduce the constituent chemicals into a signal, the processor configured to process the signal to identify specific volatile organic compounds indicative of a health condition Additionally, a wearable health monitoring device is disclosed, the wearable health monitoring device comprising a band configured to attach the wearable health monitoring device to a user's body; a VOC detection device configured to collect and analyze volatile organic compounds given off from the user's skin to identify specific health-indicative volatile organic compounds indicative of a health condition; and a biomarker sensor configured to detect a biomarker of the user.

A method of monitoring a user's health is disclosed, the method comprising collecting volatile organic compounds from a user with a collector material of a collector; separating a mixture of the volatile organic compounds into its constituent chemicals with a gas chromatography column; transducing the constituent chemicals into a signal; and analyzing the signal to identify volatile organic compounds indicative of a health condition.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

DETAILED DESCRIPTION

Figure 1:
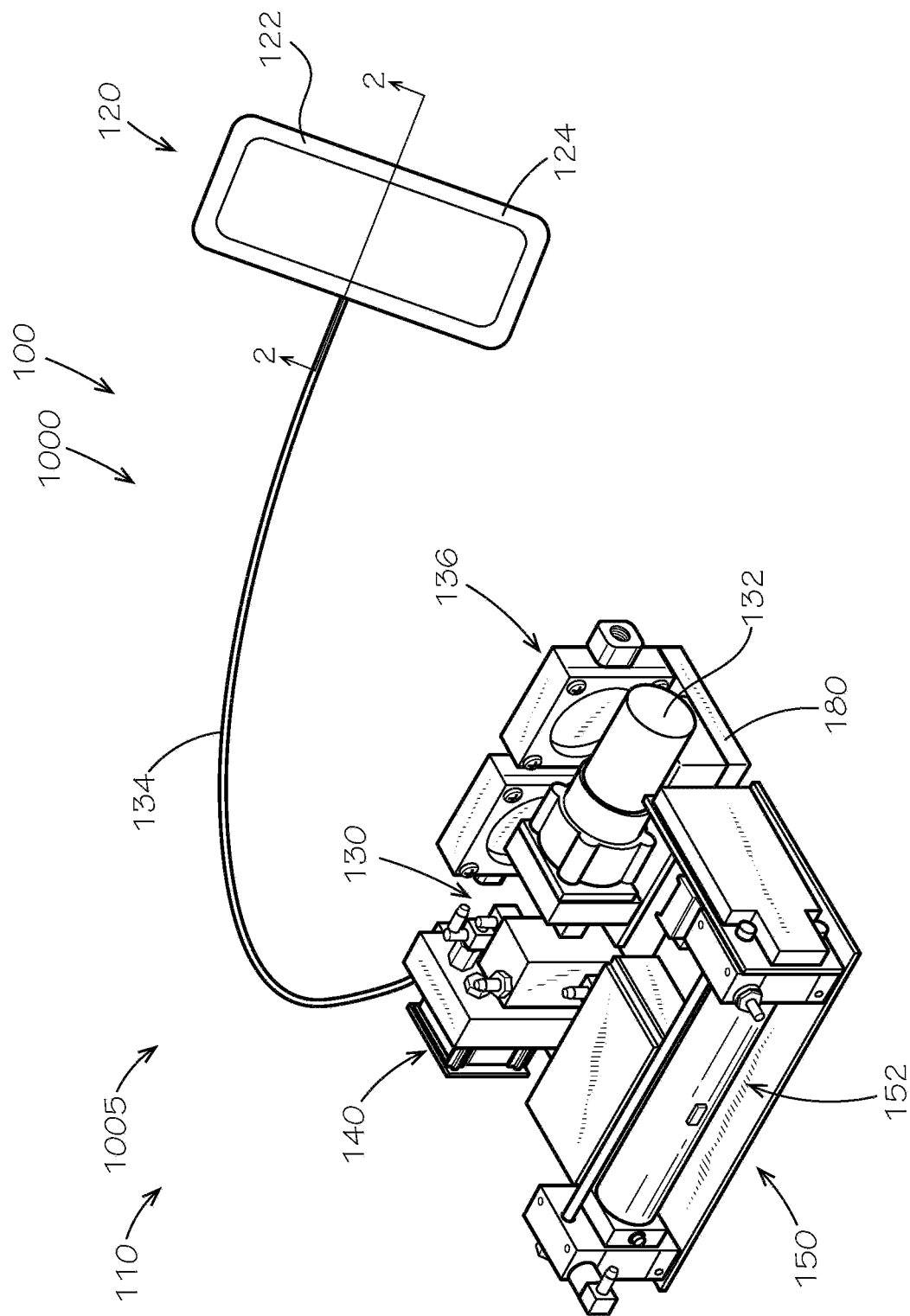
FIG. 1 is a top perspective view of a health monitoring device comprising a seizure detection device, in accordance with one aspect of the present disclosure.

The present disclosure can be understood more readily by reference to the following detailed description, examples, drawings, and claims, and the previous and following description. However, before the present devices, systems, and/or methods are disclosed and described, it is to be understood that this disclosure is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description is provided as an enabling teaching of the present devices, systems, and/or methods in its best, currently known aspect. To this end, those skilled in the relevant art will recognize and appreciate that many changes can be made to the various aspects of the present devices, systems, and/or methods described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to "an element" can include two or more such elements unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

For purposes of the current disclosure, a material property or dimension measuring about X or substantially X on a particular measurement scale measures within a range between X plus an industry-standard upper tolerance for the specified measurement and X minus an industry-standard lower tolerance for the specified measurement. Because tolerances can vary between different materials, processes and between different models, the tolerance for a particular measurement of a particular component can fall within a range of tolerances.

As used herein, the terms "optional" or "optionally" mean that the subsequently described event or circumstance can or cannot occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular aspect.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutations of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific aspect or combination of aspects of the disclosed methods.

Disclosed in the present application is a health monitoring device and associated methods, systems, devices, and various apparatus. Example aspects of the health monitoring device can comprise a band, a volatile organic compound detection device, and a biomarker sensor. It would be understood by one of skill in the art that the disclosed health monitoring device is described in but a few exemplary aspects among many. No particular terminology or description should be considered limiting on the disclosure or the scope of any claims issuing therefrom.

FIG. 1 illustrates a first aspect of a health monitoring device 1000 according to the present disclosure. In the present aspect, the health monitoring device 100 can comprise volatile organic compound detection device 1005. For example, the volatile organic compound detection device 1005 can comprise a seizure detection device 100. The seizure detection device 100 can be configured to detect specific seizure-indicative volatile organic compounds (a.k.a. VOCs, and also known as bio-volatile compounds) than can be associated with epileptic seizure onset or occurrence in human patients. In some aspects, as described in further detail below with reference to FIG. 3, the volatile organic compound detection device 1005 (henceforth, the VOC detection device 1005) can also or alternatively detect VOCs associated with other health conditions, such as, for example, migraines, stroke, stress, viral and bacterial infections, and the like. For example, the seizure-indicative VOCs can be menthone, menthyl acetate, and/or 3-ethoxy-3,7-dimethyl-1,6-octadiene, which have been identified as seizure biomarkers. In other aspects, the seizure-indicative VOCs can be any other suitable compound that can be associated with seizure in human patients. In some instances, these specific seizure-indicative VOCs may be present, either individually or in any combination, before, during, or after a seizure. Volatile organic compounds (VOCs) 200 (shown in FIG. 2), including the seizure-indicative VOCs, can be emitted as gases from the human patient, for example, through the patient's skin. According to example aspects, the seizure detection device 100 can comprise a sensor device 110 that can detect and analyze VOCs 200 in a three-stage process including pre-concentration (PC), gas chromatography (GC) separation, and detection. Additionally, in some aspects, the health monitoring device 1000 can further comprise one or more biomarker sensors (shown in FIG. 3) configured to detect additional biomarkers, such as, for example, blood oxygenation, pulse, heart rate variability, blood pressure, and/or body temperature that may be altered before, during, or after a seizure.

According to example aspects, the sensor device 110 can comprise a collector 120, a separator 130, and an identifier 150. The collector 120, which can also be referred to as a skin volatile collector or SVC, can be formed as a patch 122 that can contact the patient's skin 270 (shown in FIG. 2). In one aspect, the patch 122 can be adhered to the skin 270 by an adhesive. In another aspect, the patch 122 can be applied by another fastener, such as a band or tie, or any other suitable fastener known in the art. In the pre-concentration state, the collector 120 can collect target chemicals (e.g., VOCs 200) from the environment and can reject interferents. In the present aspect, the collector 120 can comprise a chemically-clean wrapping 124 that can isolate a sorbent collector material 226 (shown in FIG. 2) from possible external environmental contaminants. The collector material 226 can be configured to collect VOCs 200 given off as a gas from the patient's skin 270, in some aspects, and may also collect other compounds. The collector material 226 can also be isolated from direct physical contact with the patient's skin 270 to minimize contamination by sweat or skin bacteria, as described in further detail below with respect to FIG. 2. According to example aspects, a heater 228 (shown in FIG. 2) can be integrated with the collector material 226 and a thermal pulse from the heater 228 can desorb the VOCs 200 (and possibly other compounds) from the collector material 226. In some aspects, the heater 228 can be configured to heat the collector material 226 to about 200° C. A pump 132 of the seizure detection device 100 can then pump the desorbed VOCs 200 through a transfer tube 134 to the separator 130. Example aspects of the transfer tube 134 can comprise a Teflon® material, or any other suitable material.

In the GC separation stage, the collected VOCs 200 can be injected into a carrier gas (not shown), such as, for example, helium or nitrogen. A small gas plug (e.g., a sample of the carrier gas and VOC mixture) can be injected into a long, rectangular flow column 340 (shown in FIG. 3) of the separator 130. According to example aspects, a valve 140 can control injection of the gas plug and the direction and flow of the gas plug through the column 340. Example aspects of the column 340 can be a μGC (micro gas chromatography) column, while in other aspects, the column 340 can be a conventional GC (gas chromatography) column. In some aspects, the column 340 can be similar to any of the aspects disclosed in U.S. Pat. No. 10,151,732, filed Jan. 11, 2016, U.S. Pat. No. 6,699,392, filed Jun. 10, 2002, and U.S. Pat. No. 6,666,907, filed Jan. 31, 2002 which are hereby incorporated by reference herein in their entireties. In some aspects, the gas plug can undergo a μGC×GC separation or a conventional GC×GC separation, which can allow for high-fidelity separations and ultra-low false alarm rates. μGC×GC separation is micro gas chromatography x micro gas chromatography separation, while GC×GC separation is a conventional gas chromatography x gas chromatography separation, both of which can also be known as two-dimensional gas chromatography. In other aspects, the gas chromatography can be one-dimensional.

According to example aspects, the column 340 can be coated with a chemically-selective film, and the chemically-selective film can be referred to as a stationary phase. As the gas plug flows through the column 340, individual chemicals from the gas plug (including individual chemicals of the VOCs 200) diffuse into and out of the stationary phase based on their solubility within the stationary phase. VOCs 200 with a low solubility can quickly flow through the channel, while VOCs 200 with high solubility can spend a relatively long time within the stationary phase. This time-delay separates the complex chemical mixture of the gas plug into its constituent chemicals and introduces valuable spatial and chemical information that is critical for positive chemical identification and false alarm reductions in the detection stage. In example aspects, the column 340 can be a silicon μGC column that can be about 160 cm in length, about 65 μm in width, and about 650 μm deep. In example aspects, heaters (e.g., metal heaters) (not shown) can be integrated with the silicon μGC column. Furthermore, the high aspect ratio silicon μGC column can fit on a die 136 that can be about 2 cm by 2 cm on each side of the die 136, which can be a significant size reduction in comparison to traditional columns. According to example aspects, the reduced size can allow for a μGC separation to be performed in under 30 seconds by heating the column 340 from 70-200+° C. at an average power of 4.5 W.

Finally, in the detection stage, the identifier 150 can sense the chemicals eluting from the column 340 and can transduce the chemical information to a recordable signal. For example, the identifier 150 can comprise an Ion Mobility Spectrometer (IMS) detector 152. In a particular aspect, the IMS detector 152 can be a CIMS (Correlation Ion Mobility Spectrometer) detector. In another particular aspect, the IMS detector 152 can be a LTCC (Low Temperature Co-fired Ceramic) CIMS detector. In other aspects, the identifier 150 can comprise a flame ionization detector (FID), a photoionization detector (PID), a pulsed discharge ionization detectors (PDID), a resonator-based detector including quartz crystal micro balances, surface acoustic wave detectors, and/or micro-fabricated cantilever based resonators, a chemiresistor, a chemicapacitor, a thermal conductivity detector (TCD), a spectroscopic detector including vacuum ultra violet (VUV), ultraviolet, visible, and/or infrared radiation detection, a mass spectrometer detection method (MS), a non-gas chromatographic separation method such as IMS (ion mobility spectrometry), IMS-MS (ion mobility spectrometry-mass spectrometry), and/or MS-MS (tandem mass spectrometry), or any other suitable detector known in the art. Within the IMS detector 152, the incoming chemicals can be ionized and pulled down an IMS drift tube (not shown) by a potential gradient. In some aspects, the IMS drift tube can be similar to the drift tube disclosed in U.S. Pat. No. 7,155,812, filed Sep. 4, 2003, which is hereby incorporated by reference herein in its entirety.

Because the IMS detector 152 can operate at atmospheric pressures, the ionization of the chemicals can be considered a "soft" ionization, in that it minimizes the breakup or fragmentation of the chemicals. The ionized chemicals (also known as ions) can be drawn into the IMS drift tube, and the IMS drift tube can contain a faraday cup detector (not shown) at an end thereof that can count the ionic charge. The speed at which an ion travels down the IMS drift tube is a function of the ion's size, charge, and the interactions between the ion and other molecules in the IMS drift tube. Careful measurement of a characteristic transit speed down the IMS drift tube, called a reduced mobility value (or $K_o$), of a parent ion and its adducts can positively identify the target species (e.g., the specific seizure-indicative VOCs associated with seizures). In example aspects, the seizure detection device 100 can comprise a processor (not shown), for example, on a printed circuit board (PCB), for processing the data and determining whether one or more of the seizure-indicative VOCs is present. According to example aspects, a battery 180, such as a lithium ion battery, or another power source can be provided for powering the sensor device 110, including the processor.

When detection of one or more of the seizure-indicative VOCs is made, or detection of a significant concentration of one or more of the seizure-indicative VOCs is made, the processor can activate a signal. In some aspects, the signal can sound an immediate alarm to alert a patient that a seizure may be imminent. In some aspects, the signal can also or alternatively be sent wirelessly (e.g., via Bluetooth) to an external receiving unit, such as an application (also known as an app) on a cellular phone, smartphone, tablet, or other electronic instrument, to activate an additional alarm. In some instances, there can be enough forewarning to introduce an abortive therapy for the oncoming seizure. Furthermore, in some aspects, the seizure detection device 100 can also alert a caregiver or emergency personnel. Memory can be included in the application and/or the device 100 itself that can profile levels of seizure-indicative VOC concentration, duration, and the time and date of occurrence. This data can then be used as a diary of seizure activity for later review by the patient or a physician. In some aspects, the data can also be used to better predict future seizures based on the patient's individual chemistry pre-seizure. For example, in one aspect, the seizure detection device 100 may detect a slightly elevated concentration of menthone in the patient before multiple seizure occurrences. The processor can analyze this data to detect the pattern of increased menthone pre-seizure, and can identify increased menthone as a seizure-indicative VOC in the patient. The seizure detection device 100 can then alert the patient any time menthone, or a significant concentration of menthone, is detected.

Figure 2:
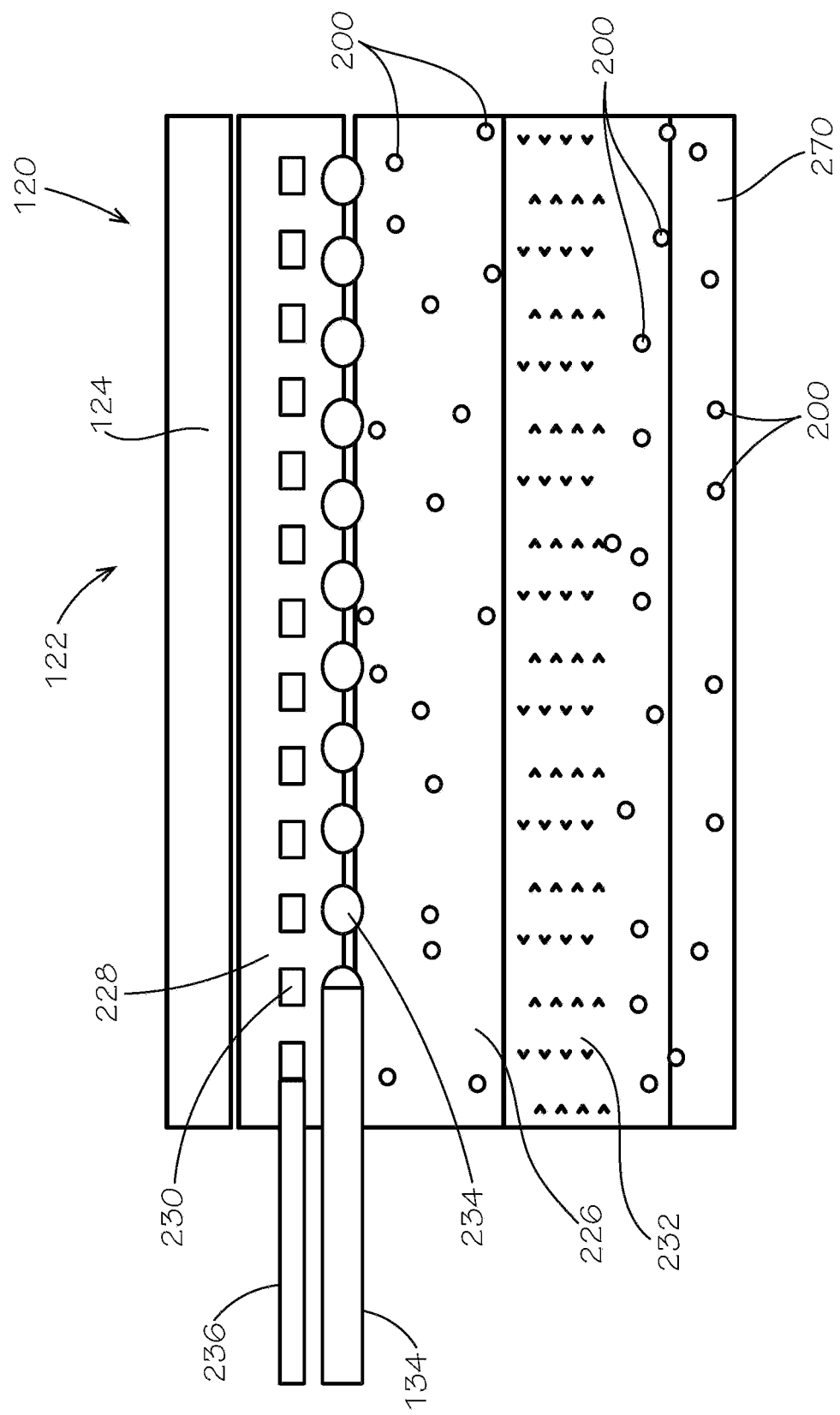
FIG. 2 is a cross-sectional view of a collector of the seizure detection device of FIG. 1, taken along line 2-2 of FIG. 1.

FIG. 2 illustrates a cross-sectional view of the collector 120 taken along line 2-2 of FIG. 1. As shown, the collector 120 can be applied to the skin 270 of a patient. The chemically-clean wrapping 124 can define an outer layer of the collector 120. In some aspects, the chemically-clean wrapping 124 can be a polyimide film, and in the present aspect, the wrapping 124 can be a polyimide film with a silicone adhesive. In other aspects, any other suitable adhesive or other fastener can be used. The collector material 226 can define an intermediate layer of the collector 120, and in the present aspect, the collector material 226 can be formed from PDMS (polydimethylsiloxane), which is a type of silicone, for example and without limitation. In the present aspect, the heater 228 can be attached to the wrapping 124, and can be positioned between the wrapping 124 and the collector material 226, as shown. In other aspects, the heating element of the heater 228 can be integrated with the wrapping 124. Furthermore, a mesh 232 can define an inner layer of the collector 120 and can be positioned between the collector material 226 and the patient's skin. Example aspects of the mesh can be formed from a polymer, such as polytetrafluoroethylene (PTFE). In other aspects, the mesh can be formed from a metal material or any other suitable material known in the art. The mesh 232 can prevent the collector material 226 from contacting the patient's skin and being contaminated by sweat, oils, and bacteria from the skin, and/or other undesirable elements.

In other aspects, the collector 120 can be configured to collect VOCs 200 through a patient's sweat, saliva, breath (e.g., exhalation), or any other suitable bodily process. Also in other aspects, the seizure-indicative VOCs can further or alternatively include β-bourbonene, β-cubebene, or any other suitable VOC that may be identified as a seizure biomarker. Furthermore, in some aspects, instead of being in contact with the patient's skin, the collector can be positioned near the patient (e.g., next to a patient's chair or bed, or elsewhere in a patient's room) and can be configured to collect VOCs from the ambient air surrounding the patient, which have been released into the air through the patient's skin and/or through the patient's exhalation.

Example aspects of the heater 228 can comprise a heating coil 230 configured to emit a thermal pulse, which can desorb VOCs 200 received in the collector material 226 into a flow channel(s) 234 between the heating coil 230 and the collector material 226. In example aspects, a power cord 236 can be connected to the heater 228 to provide power to the heating coil 230. In some aspects, the power cord 236 can be connected to the battery 180 or other power source to transfer power to the heating coil 230. When the VOCs 200 are desorbed from the collector material 226 and into the flow channel 234, the pump 132 can then sweep the VOCs 200 out of the flow channel 234 and through the transfer tube 134 to the separator 130 (shown in FIG. 1).

The seizure detection device 100 can allow patients to position themselves such that they can avoid accident, injury, embarrassment, and unnecessary trips to the emergency room. In some aspects, the seizure detection device 100 can also alert families, friends, and medical personnel to oncoming seizures, potentially reducing the amount of prophylactic medications need by patients on a daily basis. As many of these medications can be toxic and accompanied by unpleasant, occasionally life-threatening side effects, any reduction in daily dosage can result in vast improvements in patient wellbeing and functionality. Furthermore, the predictive seizure detection device 100 can allow for the development of rescue protocols in some aspects, which could reduce the severity of an oncoming seizure or, in some instances, prevent onset altogether, thus reducing or avoiding the damage that seizures can cause to the brain and the body of the patient.

Evidence indicates the presence of these seizure-indicative VOCs during the preictal (i.e., pre-seizure) stage, building in different patients at different times and at different levels of concentration based on the individual patient's metabolism and blood chemistry. Consequently, the timing of a predictive alert issued by the seizure-protection device 100 can necessarily vary from patient to patient. As a form of reference, the seizure-indicative VOCs can remain in the patient's system anywhere from about five to forty minutes postictal (i.e., post-seizure) based on the individual's metabolism.

Example aspects of the seizure detection device 100 can be on a small enough scale that the seizure detection device 100 can be easily transported with a patient as they go about daily activities, including working, exercising, eating, and sleeping. As such, various elements of the seizure detection device 100 (e.g., the column 340, the processor, etc.) can be formed as miniature or micro versions of such elements.

In addition to seizures and epilepsy, many additional health conditions create their own unique combination of specific health-indicative volatile organic compounds 200, the identification and detection of which can allow for prophylactic or palliative treatments of additional health concerns. According to example aspects, the VOC detection device 1005 can be configured to monitor specific VOCs 200 associated with additional health conditions. In some aspects, the health monitoring device 1000 can also be configured to monitor other biomarkers, such as blood oxygenation, blood pressure, pulse, heart rate variability, blood pressure, and body temperature, to allow for unprecedented efficacy and efficiency of health care.

Figure 3:
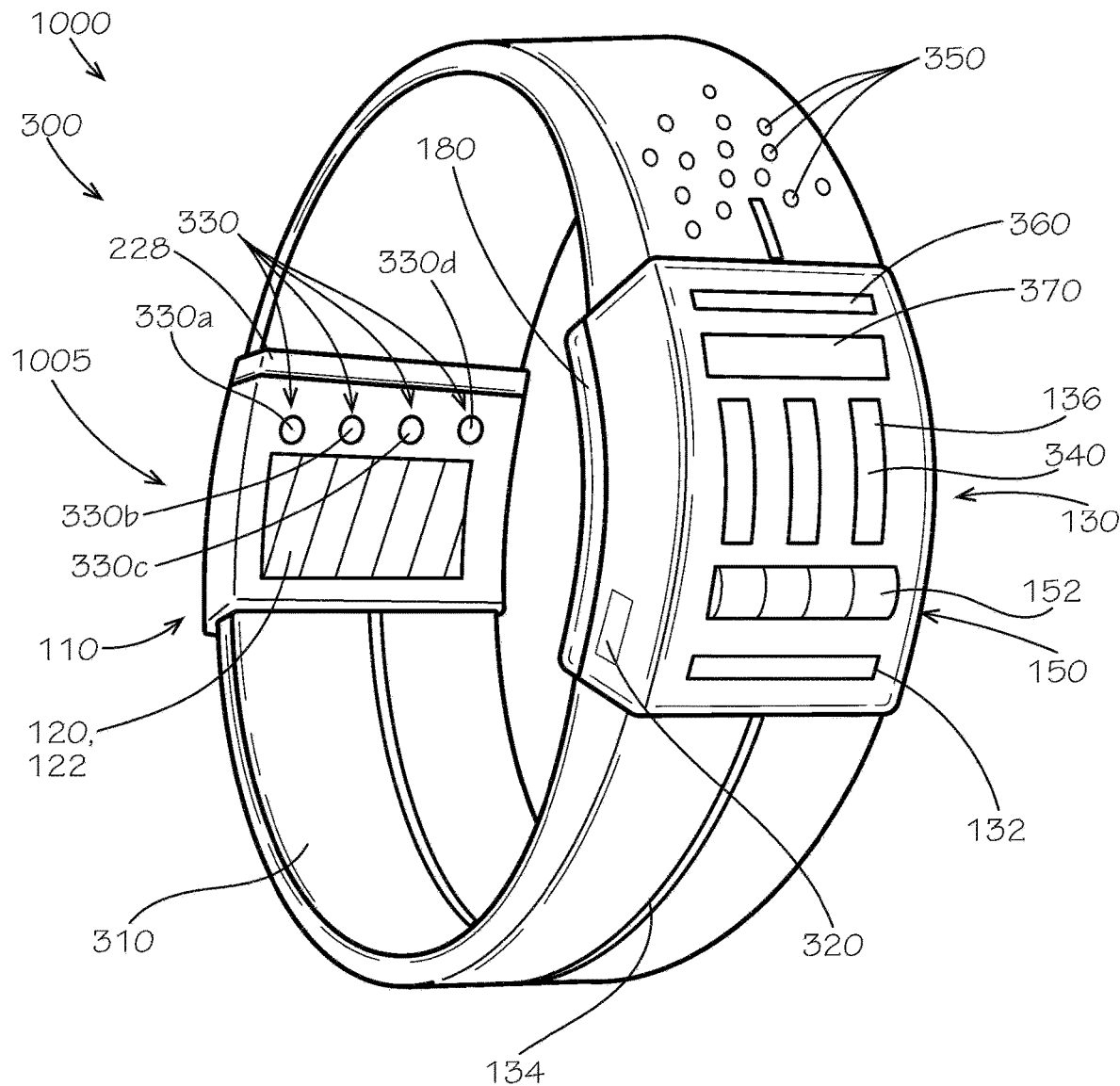
FIG. 3 is a perspective view of the health monitoring device in accordance with another aspect of the present disclosure.

FIG. 3 illustrates the health monitoring device 1000 in accordance with another aspect of the present disclosure. In the present aspect, the health monitoring device 1000 can be a wearable health monitoring device that can be attached to a user's body. For example, the health monitoring device 1000 can be a health monitoring wrist band 300, as shown, arm band, or the like. The health monitoring wrist band 300 can be configured as a watch, a bracelet, or the like. According to example aspects, the health monitoring wrist band 300 can comprise the VOC detection device 1005 and can be configured to detect and analyze specific volatile organic compounds 200 (shown in FIG. 2) indicative of seizures and/or other health conditions, including but not limited to, migraines, strokes, stress, viral infections, and/or bacterial infections. In some aspects, the VOC detection device 1005 can comprise the seizure detection device 100 (shown in FIG. 1) that can detect and analyze the seizure-indicative VOCs 200, as well as other health-indicative VOCs 200, emitted from a user.

As shown, the health monitoring wrist band 300 can comprise a band 310 configured to wrap around and attach the health monitoring device 1000 to a user's wrist, allowing the user to easily transport the health monitoring device 1000 with them wherever they go. In other aspects, the band 310 can be configured to wrap around the user's arm, leg, ankle, chest, or any other suitable body part. According to example aspects, the health monitoring wrist band 300 can comprise the battery 180 or other power source, such as a lithium ion battery, for powering the health monitoring device 1000. As shown, a charging port 320 can be provided for recharging the battery 180. Example aspects of the health monitoring wrist band 300 can comprise the sensor device 110 for collecting the VOCs 200. The collector 120, also known as the skin volatile collector, and the heater 228 of the sensor device 110 are visible in the present aspect. In the present aspect, the collector 120 can be formed as the patch 122 that can contact the user's skin 270 (shown in FIG. 2). In some aspects, the patch 122 can be configured to contact either the inside (palmar side) or the outside (dorsal side) of the user's wrist.

As described above, the sensor device 110 can be configured to collect VOCs 200, which can then be analyzed to determine the presence and/or levels of specific VOCs associated with various health conditions. In example aspects, the sensor device 110 can comprise additional biomarker sensors 330 for detecting additional biomarkers. The additional biomarkers can be monitored for detection of seizures and/or other health conditions, or can simply be monitored for informational purposes. In the present aspect, the additional biomarker sensors 330 can comprise a temperature sensor 330a for detecting temperature, a heart rate sensor 330b for detecting pulse and/or heart rate variability, a blood pressure sensor 330c for detecting blood pressure, and a blood oxygen sensor 330d (e.g., a pulse oximeter) for detecting blood oxygen level. Other aspects of the sensor device 110 can comprise fewer biomarker sensors 330 or additional biomarker sensors 330 for detecting various other biomarkers.

The health monitoring wrist band 300 can further comprise the transfer tube 134 and the pump 132 configured to pump the collected VOCs 200 through the transfer tube 134 from the collector 120 to the separator 130. As described above, the collected VOCs 200 can be injected into a carrier gas such as, for example, helium or nitrogen. In some aspects, the carrier gas can be stored in a pressurized cylinder or other gas vessel. A small gas plug (e.g., a sample of the carrier gas and VOC mixture) can be injected into the gas chromatography column(s) 340 of the separator 130. The column 340 is shown mounted to the die 136. In the present aspect, the column 340 can be a μGC×GC column, and the gas plug can undergo a two-dimensional μGC×GC separation. The identifier 150 (e.g., the IMS detector 152) can then sense the chemicals eluting from the column 340 and can transduce the chemical information to a recordable signal. In the present aspect, the IMS detector 152 can be a CIMS (Correlation Ion Mobility Spectrometer) detector. According to example aspects, the charging port 320 can also serve as a computer input port, allowing the health monitoring device 1000 to be connected to a computer to transfer the data recorded by the health monitoring device 1000 to the computer. In some aspects, the health monitoring device 1000 can also or alternatively be connected to a smart phone, tablet, or any other suitable electronic device via the charging port 320. In some aspects, the health monitoring device 1000 can be wireless connected to the computer or other electronic device.

As shown, example aspects of the health monitoring device 1000 can comprise one or more exhaust portals 350 configured to release the gas plug into the atmosphere after analysis by the identifier 150. Furthermore, according to example aspects, the health monitoring device 1000 can further comprise a display 360 configured to display information related to at least one of the collected volatile organic compounds (such as the concentration levels of the relevant VOCs) and the detected biomarker(s). For example, the display 360 can show the detected levels or indicate the presence of various health-indicative VOCs, and/or can show pulse, heart rate variability, blood oxygen level, blood pressure, temperature, and any biomarker detected by the health monitoring device 1000. In some aspects, the display 360 can display an alert message if the detected VOCs and/or biomarkers are outside of a normal range. Example aspects of the health monitoring device 1000 can further comprise a control mechanism, such as a control button 370. For example, in the present aspect, the control button 370 can be a hardware and fluid control button, which can be configured to control rebooting the health monitoring device 1000 and releasing moisture from the health monitoring device 1000 through the exhaust portals 350. In other aspects, the control button 370 can be configured to control additional or alternative aspects of the health monitoring device 1000.

In example aspects, the health monitoring device 1000 can be configured as its own platform, such as the seizure detection device 100 of FIG. 1 or the health monitoring wrist band 300 of FIG. 3. The health monitoring device 1000 can alternatively be configured as any other suitable platform, including but not limited to, a desktop unit, laptop unit, tablet unit, mobile phone unit, or the like. In some aspects, such as the desktop unit aspect, the user can swab their skin 270 (shown in FIG. 2), such as the skin on their hand, on the collector 120 to obtain a VOC sample, and the sample can be run through the desktop unit for analysis. In another aspects, a user can simply hold their skin 270 near the collector 120 to obtain the VOC sample. The varying platforms of the health monitoring device 1000 can also comprise any of the biomarker sensors 330 for detecting other biomarkers, such as body temperature, pulse, heart rate variability, blood oxygen level, and blood pressure, which can be detected by the user placing their skin (for example, the skin on their hand or wrist), against or proximate to the varying biomarker sensors 330. Furthermore, in other aspects, the health monitoring device 1000 can be integrated with an existing platform, such as an existing desktop computer, laptop computer, tablet, mobile phone, watch, or the like.

Thus, a method of monitoring a user's health can comprise collecting the volatile organic compounds 200 from a user with the collector material 226 of the collector 120, separating the mixture of the volatile organic compounds 200 into its constituent chemicals with the gas chromatography column 340, transducing the constituent chemicals into a signal, and analyzing the signal to identify the volatile organic compounds 200 that are indicative of a health condition.

The method can further comprise transferring the volatile organic compounds 200 from the collector 120 to the gas chromatography column 340, which can comprise emitting a thermal pulse from the heater 228 to desorb the volatile organic compounds 200 from the collector 120 and pumping the volatile organic compounds 200 through the transfer tube 134 from the collector 120 to the gas chromatography column 340. Example aspects of the method can further comprise detecting a biomarker of the user with the biomarker sensor 330. In some aspects, the biomarker sensor can be selected from one of the temperature sensor 330a, the heart rate sensor 330b, the blood pressure sensor 330c, and the blood oxygen sensor 330d. Additionally, in example aspects, the health monitoring device 1000 can comprise the collector 120 and the gas chromatography column 340, and can further comprise the band 310 configured to attach the health monitoring device 1000 to the user's body.

One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

It should be emphasized that the above-described embodiments are merely possible examples of implementations, merely set forth for a clear understanding of the principles of the present disclosure. Any process descriptions or blocks in flow diagrams should be understood as representing modules, segments, or portions of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A volatile organic compound detection device comprising:
   a collector comprising a collector material and an inner layer, the collector material configured to collect volatile organic compounds given off from a user's skin, the inner layer positioned between the collector material and the user's skin to prevent sweat from the user's skin from contaminating the collector material;
   a separator comprising a gas chromatography column configured to separate mixtures of the volatile organic compounds into their constituent chemicals; and
   an identifier comprising a detector and a processor, the detector configured to transduce the constituent chemicals into a signal, the processor configured to process the signal to identify specific volatile organic compounds indicative of a health condition;
   wherein the volatile organic compound detection device is a wearable health monitoring wristband comprising a band, the band configured to wrap around and attach the wearable health monitoring wristband to a user's wrist, and wherein each of the collector, the separator, and the identifier are integrally formed with and fixedly attached to the band of the health monitoring wristband.

2. The volatile organic compound detection device of claim 1, wherein the collector further comprises a heater comprising a heating element, the heating element configured to emit a thermal pulse to desorb the volatile organic compounds from the collector material.

3. The volatile organic compound detection device of claim 2, wherein the collector further comprises an outer layer, the inner layer is a mesh layer, and the collector material is received between the outer layer and the mesh layer.

4. The volatile organic compound detection device of claim 1, wherein the gas chromatography column comprises a chemically-selective film, wherein the mixtures of the volatile organic compounds are configured elute from the collector and to diffuse into and out of the chemically-selective film to separate the mixtures into their constituent chemicals.

5. The volatile organic compound detection device of claim 1, further comprising a pump and a transfer tube, the pump configured to pump the volatile organic compounds through the transfer tube from the collector to the separator.

6. The volatile organic compound detection device of claim 1, further comprising a valve configured to inject a gas plug into the gas chromatography column, wherein the gas plug comprises a carrier gas and the volatile organic compounds.

7. The volatile organic compound detection device of claim 1, wherein:
   the detector is an ion mobility spectrometer detector configured to create ionized chemicals from the constituent chemicals;
   the ionized chemicals are configured to travel through a drift tube of the ion mobility spectrometer detector; and
   the processor is configured to calculate a reduced mobility value of the ionized chemicals traveling through the drift tube.

8. The volatile organic compound detection device of claim 1, wherein the specific volatile organic compounds comprise at least one seizure-indicative volatile organic compound.

9. The volatile organic compound detection device of claim 1, further comprising a biomarker sensor configured to detect a biomarker of the user.

10. The volatile organic compound detection device of claim 1, further comprising a display configured to display information related to at least one of the specific volatile organic compounds indicative of the health condition, wherein the display is contained within the wearable device.

11. The volatile organic compound detection device of claim 1, wherein the collector material comprises silicone.

12. A volatile organic compound detection device comprising:
   a collector comprising a collector material and an inner layer, the collector material configured to collect volatile organic compounds given off from a user's skin, the inner layer positioned between the collector material and the user's skin to prevent sweat from the user's skin from contaminating the collector material;
   a separator comprising a gas chromatography column configured to separate mixtures of the volatile organic compounds into their constituent chemicals; and
   an identifier configured to identify specific volatile organic compounds from the constituent chemicals that are indicative of a health condition;
   a display configured to display information related to at least one of the specific volatile organic compounds; and
   wherein the volatile organic compound detection device is a wearable wristband configured to attach to a user's wrist, and wherein each of the collector, the separator, the identifier, and the display are contained within the wearable device;
   wherein the display is disposed at a first side of the wristband and the collector is disposed at a second side of the wristband substantially opposite the first side, the collector configured to confront a palmar side of the user's wrist.

13. A volatile organic compound detection device comprising:
   a collector comprising a collector material and an inner layer, the collector material configured to collect volatile organic compounds given off from a user's skin, the inner layer positioned between the collector material and the user's skin to prevent sweat from the user's skin from contaminating the collector material, wherein the collector material comprises silicone;
   a separator comprising a gas chromatography column configured to separate mixtures of the volatile organic compounds into their constituent chemicals; and
   an identifier comprising a detector and a processor, the detector configured to transduce the constituent chemicals into a signal, the processor configured to process the signal to identify specific volatile organic compounds indicative of a health condition;
   wherein the collector is an integral collector formed integrally with and fixedly attached to a wearable wristband of the volatile organic compound detection device.

14. The volatile organic compound detection device of claim 1, further comprising a battery and a charging port for recharging the battery.

15. The volatile organic compound detection device of claim 6, further comprising exhaust portals configured to release the gas plug into the atmosphere.

16. The volatile organic compound detection device of claim 12, wherein the identifier is disposed at the first side of the wristband, and wherein the volatile organic compounds collected by the collector are transferred from collector to the identifier through a transfer tube, the transfer tube extending along a circumferential arc of the wristband.

17. The volatile organic compound detection device of claim 1, wherein the band of the wristband defines a dorsal band section configured to confront a dorsal side of the user's wrist and a palmar band section configured to confront a palmar side of the user's wrist, and wherein the collector is integrally formed with and fixedly attached to the palmar band section of the band.

18. The volatile organic compound detection device of claim 13, wherein the integral collector is formed integrally with and fixedly attached to palmar wristband section of the wearable wristband, the palmar wristband section configured to confront a palmar side of the user's wrist.

19. The volatile organic compound detection device of claim 13, wherein the integral collector is configured to collect volatile organic compounds given off as gases from the user's skin.

\* \* \* \* \*